(12) United States Patent
Richey, Jr. et al.

(10) Patent No.: US 6,451,039 B1
(45) Date of Patent: Sep. 17, 2002

(54) MICROKERATOME BLADE ASSEMBLY

(75) Inventors: James L. Richey, Jr., Boxborough, MA (US); Detlev Gebauer, Tiefenbronn (DE)

(73) Assignee: Alcon Universal, Ltd., Fort Worth, TX (US)

( * ) Notice: Subject to any disclaimer, the term of this patent is extended or adjusted under 35 U.S.C. 154(b) by 0 days.

(21) Appl. No.: 09/648,668

(22) Filed: Aug. 25, 2000

(51) Int. Cl.[7] ............................................... A61B 17/32
(52) U.S. Cl. ...................................................... 606/166
(58) Field of Search .............................. 606/166, 167, 606/170, 180, 169, 172

(56) References Cited

U.S. PATENT DOCUMENTS

| | | | |
|---|---|---|---|
| 5,133,726 A | 7/1992 | Ruiz et al. | 606/166 |
| 5,595,570 A | 1/1997 | Smith | 606/166 |
| 5,817,115 A | 10/1998 | Nigam | 606/166 |
| 5,980,543 A | 11/1999 | Carriazo et al. | 606/166 |
| 5,989,272 A | 11/1999 | Barron et al. | |
| 6,051,009 A | * 4/2000 | Hellenkamp et al. | 606/166 |
| 6,071,293 A | * 6/2000 | Krumeich | 606/166 |

FOREIGN PATENT DOCUMENTS

| | | |
|---|---|---|
| DE | 3147662 | 6/1983 |
| EP | 1027873 A2 | 8/2000 |
| FR | 2751206 | 1/1998 |
| WO | WO 98/48748 | 11/1998 |
| WO | WO 00/ 09055 | 2/2000 |
| WO | WO 00/25711 | 5/2000 |

* cited by examiner

Primary Examiner—Kevin T. Truong
(74) Attorney, Agent, or Firm—Jeffrey S. Schira

(57) ABSTRACT

The present invention provides a microkeratome for creating lamellar sections from a biological tissue containing a blade-post assembly which improves precision and predictability by preventing undesired blade wobbling. Methods and devices are disclosed to inhibit blade wobbling, preferably frictional fittings are employed to secure the blade (or blade assembly) within the microkeratome. By biasing the blade into a secure position, wobbling during usage is substantially lessened if not eliminated. A modified blade assembly is disclosed having a post that is mated to a surgical blade. In one embodiment of the invention, the post can have one or more protrusions that engage at least one side of a recess in the microkeratome thereby creating a frictional fit sufficient to prevent movement of the blade while cutting. In another embodiment of the invention, the recess can include certain biasing elements that engage the post to prevent blade wobbling. Further, the post can contain a coupling that permits transverse oscillation of the blade while the engagement element prevents wobbling motions.

26 Claims, 5 Drawing Sheets

MICROKERATOME BLADE ASSEMBLY

BACKGROUND OF THE INVENTION

The technical field of the present invention is ophthalmic surgery and, in particular, instruments for removal of corneal tissue.

A microkeratome is a medical instrument used for resecting a thin layer of corneal tissue from the surface of the eye. In ophthalmic surgery, microkeratomes are used for various purposes. These purposes include the removal of abnormal growths in the cornea, preparation of damaged eyes for corneal transplants, preparation of eyes for other surgical procedures and direct surgical corrections of refractive disorders.

Considerable interest has been recently generated in a variety of techniques for reshaping the cornea for refractive vision correction. These techniques are based on the observation that most of an eye's refractive power is contributed by the corneal curvature itself (with the remaining refractive power being provided by the lens of the eye located inside the ocular globe). For people suffering from nearsightedness (myopia), it has been recognized that a slight flattening of the corneal curvature can correct this condition if properly applied. Conversely, correction of farsightedness (hyperopia) requires a steepening of the corneal curvature. Correction of astigmatism typically requires more complex reprofiling.

It has been suggested on a number of occasions that it is possible to correct refractive errors by mechanical sculpting of the cornea into an ideal shape and curvature. However, until very recently, there have been no tools suitable for this purpose. The anterior surface of the cornea is covered with a thin layer of epithelial tissue followed by a membrane-like structure known as Bowman's layer. Typically, Bowman's layer is about 30 micrometers thick, although it may vary from as little as 10 micrometers to over 50 micrometers in thickness.

Below Bowman's layer lies the stroma proper of the cornea. This stromal tissue is approximately 450 micrometers in thickness, although it also varies from individual to individual. Stromal tissue is composed of a highly organized matrix of acellular collagen. The Bowman's membrane that lies above it is less regular and denser.

Efforts at mechanical sculpting of the cornea have been largely unsuccessful to date because even the sharpest metal (or even diamond) blades are incapable of producing precise ablations of corneal tissue with the necessary accuracy. The irregularity of Bowman's layer is a further complicating factor that has stymied mechanical attempts at wide-area sculpting of the anterior surface of the cornea.

In an alternative surgical procedure, an anterior segment of the cornea is removed (or partially severed and displaced) by a microkeratome so that the stromal bed can be mechanically sculpted. Because Bowman's layer is removed or displaced intact in such procedures, mechanical instruments (e.g., specially designed microkeratomes and the like) have had moderate success in resculpting the stroma proper. After the stromal bed has been surgically reshaped, the anterior lenticule is replaced. Again, this procedure has the advantage of avoiding mechanically shaving Bowman's layer, albeit at the expense of a deeper penetration into the stroma.

Recently, a new procedure, known as "laser vision correction" has become available to ophthalmologists to perform corneal surgery. Laser vision correction employs high energy pulses of ultraviolet radiation, typically from excimer lasers, to ablate thin layers of corneal tissue by a process known as "photodecomposition." This laser vision correction process relies upon the ability of such laser radiation to remove extremely thin layers of corneal tissue within an exposed area without thermal damage to adjacent tissue. In one type of procedure known as photorefractive keratectomy (PRK), the laser beam is either repeatedly scanned across the cornea or otherwise controlled to expose the cornea to a beam of different shape or size over time so as to effect a cumulative reprofiling of the corneal surface.

In a particular class of PRK procedures known as Laser Assisted In Situ Keratoplasty (LASIK), a microkeratome is used to remove (or hingedly displace) an anterior lamina of the cornea (in much the same way as in the procedures that involve mechanical sculpting of the stroma) while a laser is used to selectively ablate stromal tissue. Again, like mechanical sculpting procedures, the anterior lamina is replaced following the procedure with Bowman's membrane intact. This LASIK procedure is also very promising but likewise requires precision in the removal of the lamina.

The microkeratome typically includes an eye ring assembly for placement on the ocular globe such that a portion of the cornea is secured. A cutting blade is then carried along a cutting path defined, at least in part, by the guide ring or other elements connected to the guide ring.

In ophthalmic surgery, the dimensions of the resection must be very precise and predictable. Precision can depend on several factors, including the pressure exerted by the surgeon's hands on the instrument and on the patient's eye, and the speed at which the blade is pushed to make the resection. Even when the movement of the blade is automated, there are factors that affect the precision of the cut.

Various techniques have been proposed for improving precision. For example, U.S. Pat. No. 5,980,543 to Carriazo et al. describes a microkeratome having a float arm compressing the surface of a cornea in front of the blade prior to cutting. The float arm is connected to the cutting head to, at least partially, compress the cornea ahead of the blade so as to set the desired thickness of the corneal resection. Carrizo's blade assembly is exemplary of the prior art technique for coupling a blade to the body of the keratome.

The problem of controlled movement across the guide ring is addressed in U.S. Pat. No. 5,133,726 to Ruiz et al., which discloses a microkeratome with a mechanical drive assembly that provides a uniform mechanical motion. The blade assembly disclosed in Ruiz is introduced into the cavity in such a way that the blade is held parallel to the underside of the upper body of the microkeratome.

U.S. Pat. No. 5,817,115 to Nigam discloses an alternative instrument for making corneal incisions wherein a vacuum holds the cornea in place while an incision is made by a blade sliding through the instrument. The blade is mated to and driven by a plunger which actuates within a recess in the instrument. When the plunger is forced into the instrument, a spring is put in compression thus tending to push the plunger in the direction opposite the plunger's movement. This arrangement purportedly slices the cornea in a single continuous motion.

There exists a need for better microkeratomes, generally, to facilitate both mechanical and laser vision correction procedures. A better, more accurate keratome, would allow ophthalmic surgeons to perform therapeutic keratectomies (removing small regions of corneal tissue which exhibit abnormal growths or ulcers), resections of anterior corneal segments (as a first step in keratomileusis, stromal sculpting procedures, LASIK procedures and the like) and a variety of other surgical operations on the cornea.

SUMMARY OF THE INVENTION

It has been discovered that unintended movements of the blade assembly occur during use of many microkeratomes and such movements (typically involving a "wobbling"

motion of the blade) degrade both the precision and the reproducibility of results. The source of this errant motion can be traced in many instances to the fit of a disposable blade assembly within the microkeratome body. Many commercially available microkeratomes operate with a disposable blade that is intended for use on only one patient. Following each procedure, the blade must be replaced. A conventional design provides for the blade to be bonded to a post that permits easy handling by the clinician. This blade and post assembly is commonly referred to as a "blade assembly." A number of commercially available microkeratomes are designed with a recess into which the blade assembly is placed. Although the assembly is typically designed to fit within the recess, a small amount of clearance is necessary to facilitate insertion and removal of the blade assembly. As a consequence of this clearance, the blade itself is only loosely secured during operation and largely held in place by the pressure exerted against the blade by the corneal tissue during resection.

Accordingly, methods and devices are disclosed to inhibit blade wobbling. In one aspect of the invention, frictional fittings are employed to secure the blade (or blade assembly) within the microkeratome. Various engagement elements are disclosed for immobilizing the post of a blade assembly upon insection into a microkeratome housing. The engagement elements preferably have spring-like characteristics. By biasing the blade into a secure position, wobbling during usage is substantially lessened if not eliminated.

In one aspect of the invention, a microkeratome is provided for creating lamellar sections from a biological tissue containing a blade-post assembly and at least one engagement element that improve precision and predictability by preventing undesired blade wobbling.

In another aspect of the invention, a modified blade assembly is disclosed having a post that is mated to a surgical blade. In one embodiment of the invention, the post can have one or more protrusions that engage at least one side of a recess in the microkeratome thereby creating a frictional fit sufficient to prevent movement of the blade while cutting. For example, the post can bias a portion of the blade assembly against an inner surface of the recess. In another embodiment of the invention, the recess can include certain biasing elements that engage the post to prevent blade wobbling. Further, the post can contain a coupling that permits transverse oscillation of the blade while the engagement element prevents wobbling motions.

BRIEF DESCRIPTION OF THE DRAWINGS

The invention will be more fully understood from the following detailed description taken in conjunction with the accompanying drawings, in which like reference numerals designate like parts throughout the figures, and wherein.

DETAILED DESCRIPTION OF THE DRAWINGS

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Figure 1:
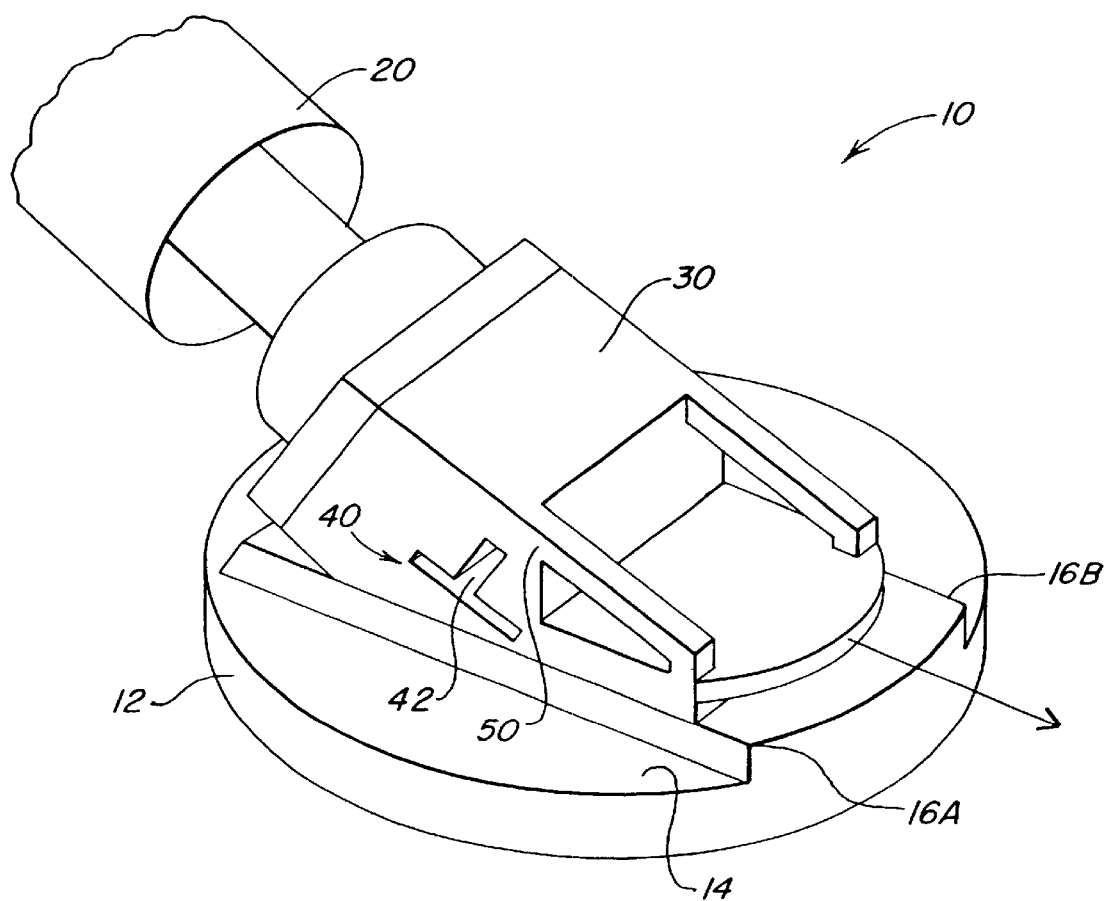
FIG. 1 is a perspective view of a microkeratome in accordance with this invention.

FIG. 1 illustrates a microkeratome 10 in accordance with the invention that includes a body portion 30, an eye ring assembly 12, and a blade assembly 40. The body 30 is fitted to the eye ring assembly 12 in such a way as to be free to slide across it. The microkeratome 10 also includes a motor 20 or similar drive mechanism. The eye ring assembly 12 can further include a platform 14 that supports and guides the body 30. The body portion 30 further includes a recess 18 that receives a blade assembly 40.

Figure 2:
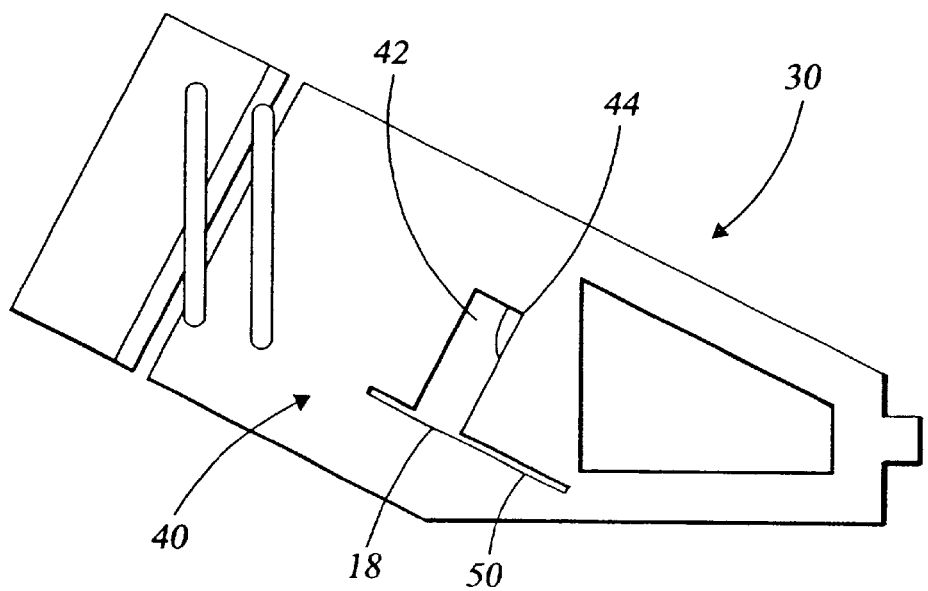
FIG. 2 is a side view of a body portion of the microkeratome of FIG. 1.

FIG. 2 is a more detailed description of the microkeratome body 30 having a blade assembly 40 which includes a blade post 42 and a cutting element 50. In accordance with the invention, the blade assembly 40 has an engagement element 44 which biases the blade assembly into a secured position and substantially lessens, if not eliminates, wobbling during usage.

Figure 3:
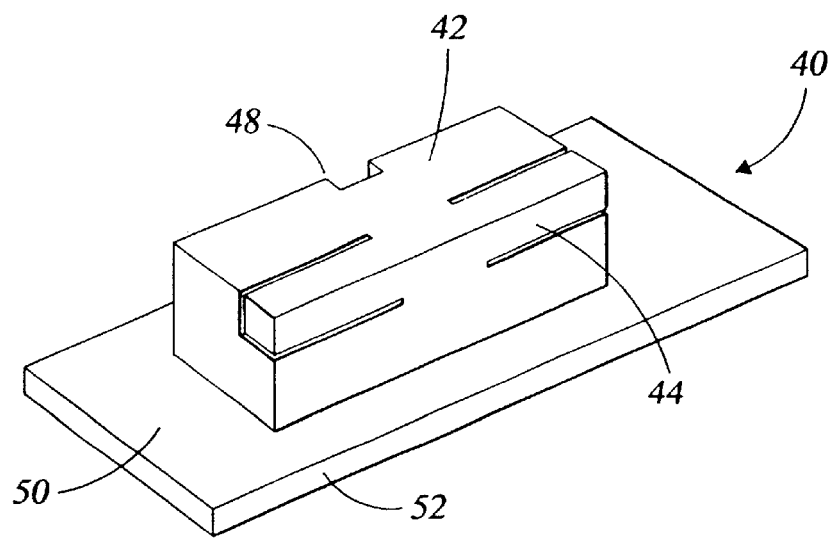
FIG. 3 is a side view of a blade assembly in accordance with the invention.
Figure 4:
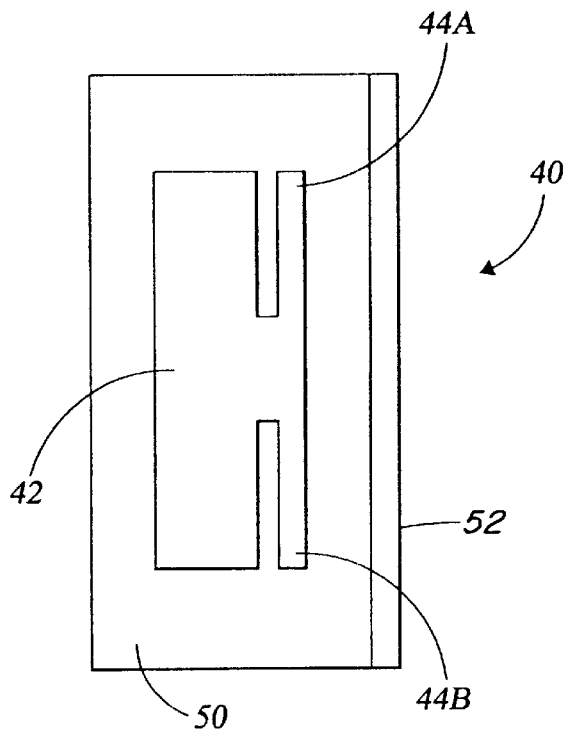
FIG. 4 is a top view of the blade assembly of FIG. 3.

FIG. 3 shows a side view of the blade assembly having a blade post 42 that is mated to a surgical blade 50 having a blade edge 52. The post has one or more protrusions that engage at least one side of a recess in the microkeratome thereby creating a frictional fit sufficient to prevent movement of the blade while cutting. FIG. 4 shows a top view of a blade assembly 40 having a blade post 42 and a cutting element 50. In this illustration, the blade post has two engagement elements 44A and 44B. The cutting element has a blade edge 52.

The blade post 42 can also contain a coupling 48 (e.g. to motor 20 of FIG. 1) that permits transverse oscillation of the blade while the engagement element prevents wobbling motions. The blade post 42 can be made from metal. In a further embodiment, the blade post 40 can be a magnetized metal post.

In use, the eye ring of FIG. 1 (or a similar platform-defining structure) is attached to the eye and the microkeratome body 30 positioned upon it. A blade assembly 40 (with its post 42 and blade 50) is slid into a recess 18 in the body 30. In accordance with the invention, the engagement element 44 secures the blade assembly 40 within the recess 18.

Figure 5:
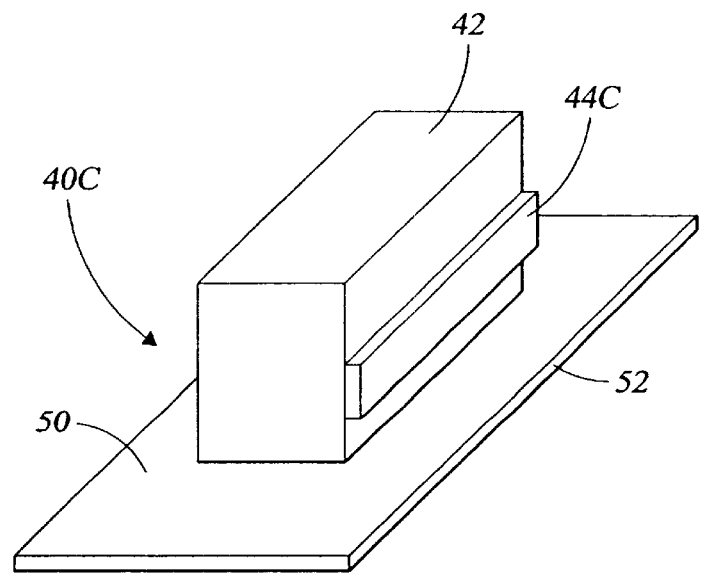
FIG. 5 is a perspective view of an alternative embodiment of a blade assembly in accordance with the invention.
Figure 6:
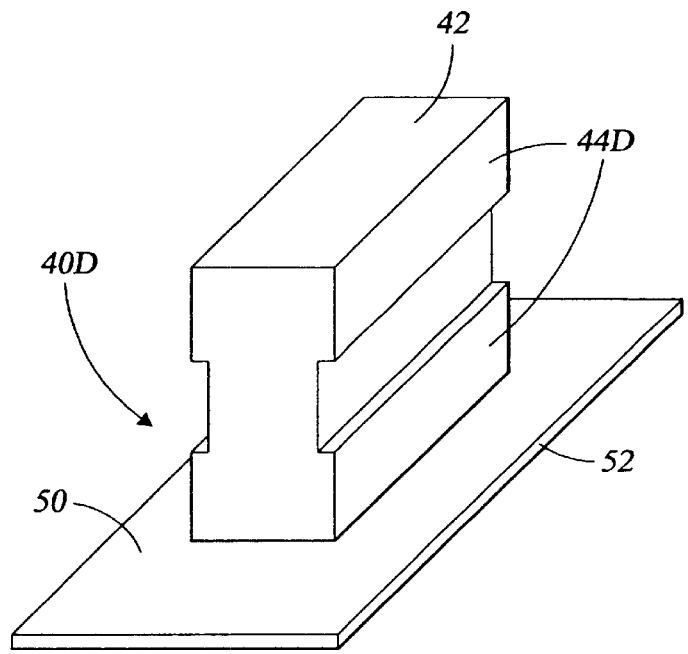
FIG. 6 is another perspective view of an alternative embodiment of a blade assembly in accordance with the invention.
Figure 7:
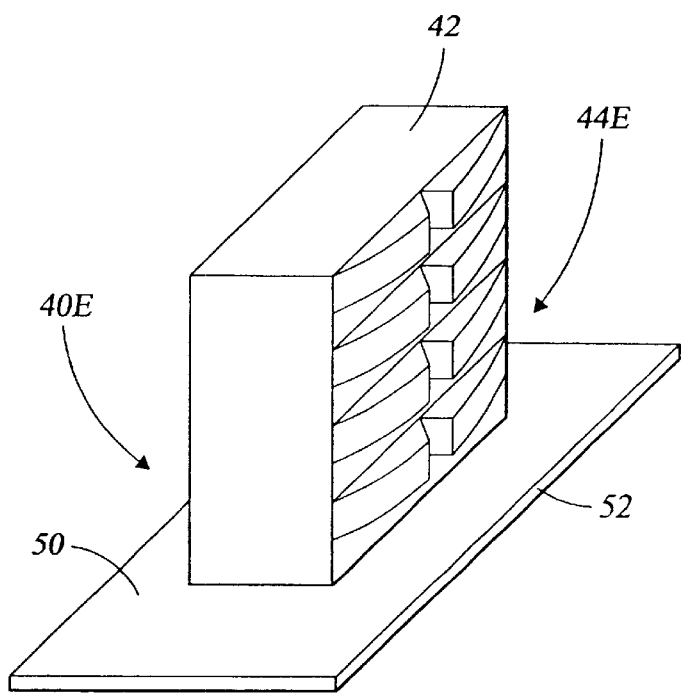
FIG. 7 is yet another perspective view of an alternative embodiment of a blade assembly in accordance with the invention.

FIGS. 5–7 show alternative blade assembly having one or more protrusions that engage at least one side of a recess in the microkeratome thereby creating a frictional fit sufficient to prevent movement of the blade while cutting. In FIG. 5, a blade assembly 40C is shown having an engagement element 44C formed as a horizontal strip, which can be formed by attachment of an elastomeric strip material, or by machining of the part 42 itself. Alternatively, strip 44C can be a magnet or magnetic material. In FIG. 6, a plurality of horizontal biasing strips 44D are provided, e.g., by machining slots in the post 42. In FIG. 7 a plurality of bow shaped engagement elements 44E are shown, which again can be formed by joining one or more biasing elements to the post 42 or by appropriate machining of the post 42.

Figure 8:
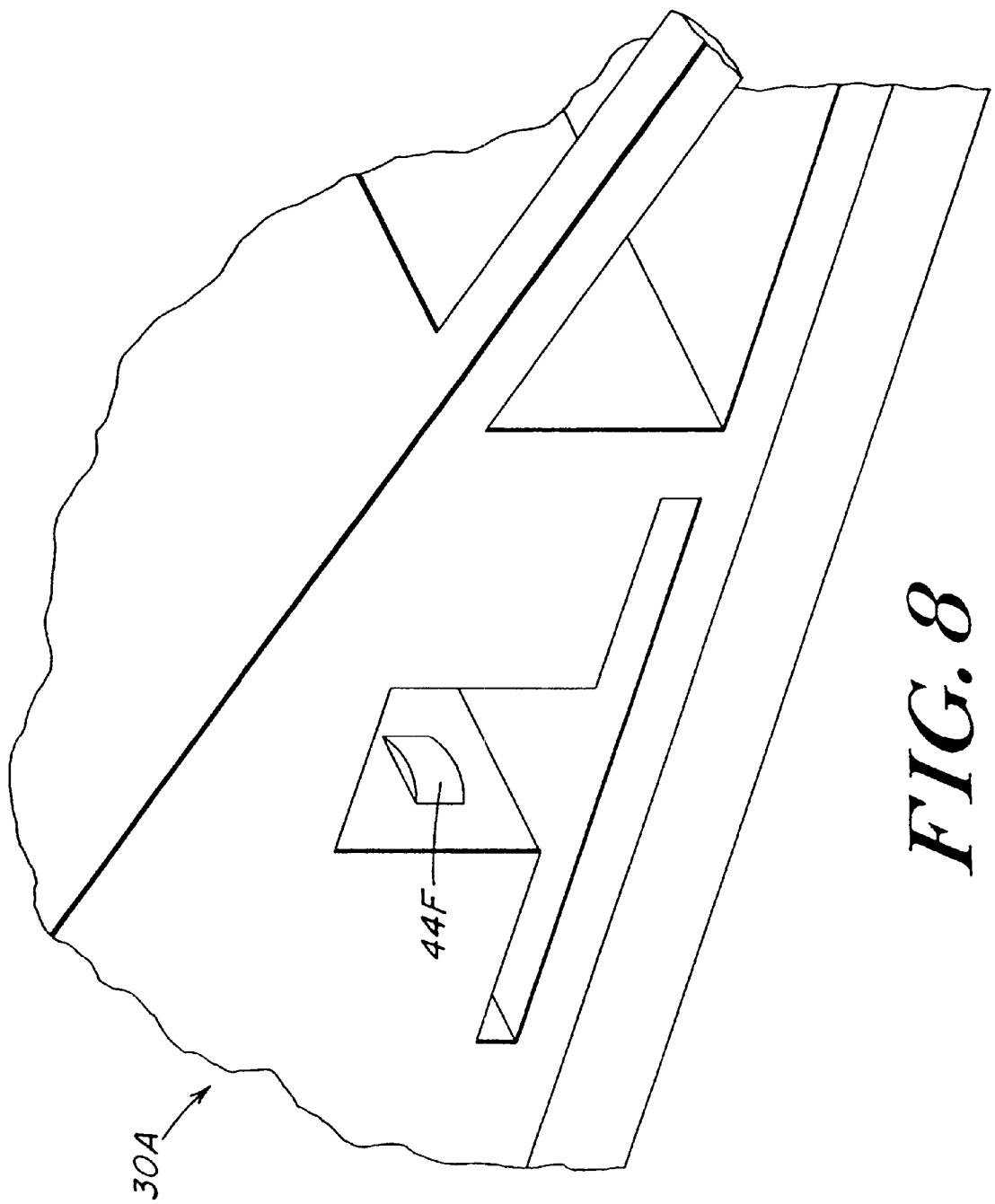
FIG. 8 is a partially cut away, perspective view of a microkeratome body incorporating an alternative biasing element according to the invention.

FIG. 8 shows a partial view of the body wherein the recess 18 includes certain biasing elements 44F that engage the blade post to prevent wobbling.

Although a number of engagement elements are illustrated herein, it should be clear that various other mechanisms can be employed to create a frictional fit or otherwise engage the blade within the microkeratome to prevent movement of the blade while cutting. As noted above, the engagement element can be a deformable protrusion. The deformable protrusion can either be on the blade assembly or placed inside the recess itself. In another embodiment, the engagement element is a slot in the post that facilitates deformation of the post upon insertion. The engagement element can also be a plurality of strips or bands. In some applications, it is preferable for the engagement member to exhibit spring-like characteristics (e.g. respond to a compressive force in accordance with the formula: $F=½\ K\ x^2$) while in other applications magnetic or electromagnetic forces can be employed to engage the blade.

What is claimed is:

1. A microkeratome for creating lamellar sections from a biological tissue, comprising:

a housing comprising a recess;

a blade assembly removably disposed within the recess and including a blade and a post; and at least one engagement element formed on at least one of the recess and the post to provide a frictional fitting between the post and at least one wall of the recess when the blade assembly is disposed within the housing.

2. The microkeratome of claim 1, wherein the engagement element biases a portion of the blade assembly against an inner surface of the recess.

3. The microkeratome of claim 1, wherein:

the blade has a first surface;

the post is attached to a portion of the first surface of the blade, the post being dimensioned to substantially correspond to the recess of the microkeratome; and the at least one engagement element is associated with the post, such that upon insertion of the post and the attached blade into the recess, the engagement element abuts at least one interior surface of the recess to confine the post within the recess.

4. The device of claim 3, wherein the engagement element comprises at least one deformable element.

5. The device of claim 3, wherein the engagement element comprises at least one slot in the post that facilitates deformation of the post upon insertion.

6. The device of claim 3, wherein the engagement element comprises a plurality of deformable strips.

7. The device of claim 3, wherein the post further comprises a coupling that permits transverse oscillation of the blade, the engagement element permitting the oscillation while inhibiting undesired wobbling motions.

8. The microkeratome of claim 3, wherein the engagement element further comprises a deformable tab.

9. The microkeratome of claim 8, wherein the deformable tab is partially separated from the post.

10. The microkeratome of claim 9, wherein the tab is separated from the post body by an L-shaped slot.

11. The microkeratome of claim 3, wherein the microkeratome further comprises at least two engagement elements formed by deformable tabs which are partially separated from the post by slots.

12. The microkeratome of claim 11, wherein each of the tabs further comprise a protrusion for contacting at least one side of the recess.

13. The device of claim 1, wherein the engagement element comprises a magnetic material.

14. The microkeratome of claim 1, further comprising:

an eye ring having formed on one surface thereof a series of tracks; and a motor for driving the blade housing along the tracks on the eye ring.

15. A microkeratome for creating lamellar sections from a biological tissue, comprising:

a blade housing for receiving a blade assembly, the housing defining a recess therein;

a blade assembly insertable into the recess, the blade assembly including a post, a blade and at least one engagement element formed on one of the recess and the post to provide a frictional fitting between the post and at least one wall of the recess when the blade assembly is disposed within the housing;

an eye ring having disposed thereon a plurality of tracks; and a motor removably connected to the blade housing for driving the blade housing along the tracks on the eye ring.

16. A disposable blade assembly, comprising:

a blade;

a post attached to a portion of a first surface of the blade, the post being dimensioned to substantially correspond to a recess of a microkeratome; and at least one engagement element formed on the post, such that upon insertion of the post and the attached blade into the recess, the engagement element provides a frictional fitting between the post and at least one wall of the recess to confine the post within the recess.

17. The device of claim 16, wherein the engagement element comprises at least one deformable element.

18. The device of claim 16, wherein the engagement element comprises at least one slot in the post that facilitates deformation of the post upon insertion.

19. The device of claim 16, wherein the engagement element comprises a plurality of deformable strips.

20. The device of claim 16, wherein the engagement element comprises a magnetic material.

21. The device of claim 16, wherein the post further comprises a coupling that permits transverse oscillation of the blade, the engagement element permitting the oscillation while inhibiting undesired wobbling motions.

22. The device of claim 16, wherein the engagement element further comprises a deformable tab.

23. The device of claim 22, wherein the deformable tab is partially separated from the post.

24. The device of claim 23, wherein the tab is separated from the post body by an L-shaped slot.

25. The device of claim 16, wherein the microkeratome further comprises at least two engagement elements formed by deformable tabs which are partially separated from the post by slots.

26. The device of claim 25, wherein each of the tabs further comprise a protrusion for contacting at least one side of the recess.

* * * * *